(12) United States Patent
Silhavy

(10) Patent No.: US 12,383,917 B2
(45) Date of Patent: Aug. 12, 2025

(54) DUAL RESERVOIR SPRAY DISPENSER

(71) Applicant: Coty Inc., New York, NY (US)

(72) Inventor: Christophe Silhavy, Levallois-Perret (FR)

(73) Assignee: Coty Inc., New York, NY (US)

( * ) Notice: Subject to any disclaimer, the term of this patent is extended or adjusted under 35 U.S.C. 154(b) by 122 days.

(21) Appl. No.: 18/001,027

(22) PCT Filed: May 20, 2021

(86) PCT No.: PCT/US2021/033387
§ 371 (c)(1),
(2) Date: Dec. 7, 2022

(87) PCT Pub. No.: WO2022/010578
PCT Pub. Date: Jan. 13, 2022

(65) Prior Publication Data
US 2023/0149961 A1 May 18, 2023

Related U.S. Application Data

(60) Provisional application No. 63/048,283, filed on Jul. 6, 2020.

(51) Int. Cl.
*B05B 7/24* (2006.01)
*A61K 8/04* (2006.01)
(Continued)

(52) U.S. Cl.
CPC .......... *B05B 11/1084* (2023.01); *A61K 8/046* (2013.01); *A61Q 19/00* (2013.01);
(Continued)

(58) Field of Classification Search
CPC ....... B05B 11/1084; B05B 7/24; A61K 8/046; A61K 2800/10; A61K 2800/882; A61Q 19/00
See application file for complete search history.

(56) References Cited

U.S. PATENT DOCUMENTS 4,773,562 A * 9/1988 Gueret .................... B01F 25/31
222/145.6
4,792,062 A * 12/1988 Goncalves ............. B65D 83/68
239/353
(Continued)

FOREIGN PATENT DOCUMENTS

| CN | 115942997 | 4/2023 |
| EP | 3025614 A1 | 6/2016 |

(Continued)

OTHER PUBLICATIONS

"International Application Serial No. PCT US2021 033387, International Preliminary Report on Patentability mailed Jan. 19, 2023", 7 pgs.

(Continued)

*Primary Examiner* — Frederick C Nicolas
(74) *Attorney, Agent, or Firm* — Schwegman Lundberg & Woessner, P.A.

(57) ABSTRACT

A dual reservoir spray dispenser can separately hold two different components, while jointly dispensing the two different components as a sprayable composition. A common actuator of the dual reservoir spray dispenser can include a pipe (2) having a sinuous path. The pipe can include two inlet orifices (3, 5) and an outlet orifice (4).

14 Claims, 4 Drawing Sheets

(51) Int. Cl.
  *A61Q 19/00* (2006.01)
  *B05B 11/10* (2023.01)
(52) U.S. Cl.
  CPC ............ *B05B 7/24* (2013.01); *A61K 2800/10* (2013.01); *A61K 2800/882* (2013.01)

(56) References Cited

U.S. PATENT DOCUMENTS

| | | | | |
|---|---|---|---|---|
| 5,332,157 | A * | 7/1994 | Proctor | B05B 11/1083 239/304 |
| 5,398,846 | A * | 3/1995 | Corba | B05B 11/0044 222/145.5 |
| 5,402,916 | A * | 4/1995 | Nottingham | B05B 11/1011 222/134 |
| 5,611,463 | A * | 3/1997 | Favre | B05B 11/028 222/137 |
| 5,632,413 | A * | 5/1997 | Herring, Jr. | F16B 11/006 222/509 |
| 6,308,863 | B1 * | 10/2001 | Harman | B65D 83/68 239/304 |
| 6,454,135 | B1 * | 9/2002 | Brozell | B05B 11/1011 222/162 |
| 6,672,483 | B1 * | 1/2004 | Roy | B05B 11/1084 222/136 |
| 7,490,743 | B2 * | 2/2009 | Herzog | G01F 11/028 222/321.7 |
| 7,906,473 | B2 * | 3/2011 | Williams | D06L 4/18 510/303 |
| 8,474,659 | B2 * | 7/2013 | Dennis | B05B 11/1084 222/137 |
| 8,544,495 | B1 | 10/2013 | Weingart et al. | |
| 9,579,676 | B1 * | 2/2017 | Burrowes | A61L 9/14 |
| 9,757,754 | B2 * | 9/2017 | Burrowes | B05B 7/0408 |
| 9,839,931 | B2 * | 12/2017 | Burrowes | B01F 25/102 |
| 9,931,657 | B2 * | 4/2018 | Gonzalez | B05B 11/1014 |
| 10,029,267 | B2 * | 7/2018 | Connolly | A45D 34/02 |
| 2004/0063600 | A1 | 4/2004 | Williams et al. | |
| 2015/0354550 | A1 * | 12/2015 | Burrowes | B05B 1/3436 137/565.33 |
| 2017/0065993 | A1 | 3/2017 | Burrowes et al. | |
| 2017/0151579 | A1 | 6/2017 | Connolly et al. | |

FOREIGN PATENT DOCUMENTS

| | | |
|---|---|---|
| EP | 4175758 B1 | 12/2024 |
| EP | 4311604 B1 | 12/2024 |
| WO | WO-2022010578 A1 | 1/2022 |

OTHER PUBLICATIONS

"European Application Serial No. 21737217.6, Communication Pursuant to Article 94(3) EPC mailed Oct. 25, 2023", 3 pgs.

"European Application Serial No. 21737217.6, Response filed Nov. 22, 2023 to pursuant to Communication Pursuant to Article 94(3) EPC mailed Oct. 25, 2023", 59 pgs.

"European Application Serial No. 23215302.3, Extended European Search Report mailed Mar. 4, 2024", 6 pgs.

"European Application Serial No. 23215302.3, Response filed Apr. 22, 2024 to Extended European Search Report mailed Mar. 4, 2024", 8 pgs.

"European Application Serial No. 21737217.6, Communication Pursuant to Article 94(3) EPC mailed Jan. 19, 2024", 2 pgs.

"International Application Serial No. PCT/US2021/033387, International Search Report mailed Sep. 13, 2021", 6 pgs.

"International Application Serial No. PCT/US2021/033387, Written Opinion mailed Sep. 13, 2021", 5 pgs.

* cited by examiner

DUAL RESERVOIR SPRAY DISPENSER

CROSS REFERENCE TO RELATED APPLICATION

This application is a U.S. National Stage Filing under 35 U.S.C. 371 from International Application No. PCT/US2021/033387, filed on May 20, 2021, and published as WO 2022/010578 on Jan. 13, 2022, which application claims the benefit of priority of U.S. Provisional Patent Application No. 63/048,283, filed on Jul. 6, 2020, the benefit of priority of which is claimed hereby, and which is incorporated by reference herein in its entirety.

TECHNICAL FIELD

The present invention relates to dual reservoir spray dispenser, systems, kits and methods thereof.

BACKGROUND

In the consumer good industry, sprayable products e.g. liquid compositions are customarily packaged in a spray dispenser comprising a container for holding the product to be sprayed, a pump unit and an actuator assembly, including for example a push button and a nozzle tip, for dispensing the product in the form of a spray. Such spray dispensers are commercialized in numerous technical fields e.g. in skin care, hair care, personal care, grooming, oral care, health care, fabric care, home care, etc.

The products to be sprayed are usually pre-formulated, ready-to-use products, and exhibit a good stability over time. The dispensers filled with the products may therefore be shelved and/or used during several months or even years.

However, some products are not stable over time and require to be mixed just prior being dispensed. The lack of stability may be due to various reasons such as the inherent instability of a compound e.g. the degradation upon oxygen and/or light exposure, the incompatibilities of some compounds together e.g. their immiscibility, the degradation of a compound by another, the chemical reaction of two compounds together, etc.

Nowadays, it is cumbersome and unpractical for the users to formulate themselves the products to be sprayed just prior use. Dispensers comprising at least two reservoirs for storing separately two components to be mixed upon use and co-dispensed as a spray are known. Particularly, dual reservoir spray dispensers, comprising separate reservoirs and separate corresponding pump units, have been used for many years.

When designing a dual reservoir spray dispenser, several constraints need to be tackled, including both technical, aesthetical and ergonomic constraints. Particularly, in fields where the visual appearance matters such as in cosmetics, the aesthetics of the packaging should not be at the expense of the ergonomics and the technical performance. Indeed, a satisfactory user's experience depends on a visually pleasing packaging being handy to grasp and to co-dispense the sprayable components. Such a packaging may also have a long-lasting efficacy and may be used over several months or even more than a year from the first to the last spray e.g. fragrance packaging comprising microcapsules and a volatile solvent.

On an aesthetical standpoint, the user particularly appreciates a packaging wherein both reservoirs are located side-by-side, instead of one-behind-the-other, such that, upon use, both containers are visible to the user when grasped in the user's hand. In such type of assembly, if the packaging is hold vertically with the push button atop the reservoirs, the spray direction is substantially perpendicular to the vertical plan passing by both reservoirs and the corresponding pump units.

Different actuator assemblies have been designed in order to dispense and spray the components. For example, the actuator assembly may comprise two separate pipes with outlet orifices being located close to each other, such that the mixing of the components—so-called in-flight mixing—only occurs when being dispensed from the outlet orifices. Alternatively, the actuator may comprise two separate pipes respectively in fluid communication with the corresponding pump units, both pipes reaching a common pipe wherein both components are mixed before being dispensed. The path of the separate pipes and the common pipe may vary and may have for example a T-shape (the common path forming a straight angle with the separate pipes) or a Y-shape (the common path forming an obtuse angle e.g. from 120 to 150° with the separate pipes).

Spray dispensers with side-by-side reservoirs of the above types are visually pleasing packaging being handy to grasp and to co-dispense the sprayable product. However, the user's experience is not completely satisfactory as the quality and the efficacy of the spraying may be altered over time such as for dispensers being used over a long period of time e.g. fragrance packaging, particularly packaging comprising fragrance-loaded microcapsules. Particularly, after a certain number of sprays and/or after a certain amount of time, the pipes may get partly or fully clogged and the dispenser should then be discarded before the reservoirs are emptied. Clogging may be due to various reasons including the drying of at least one of the components and/or the mixture, the decompositions of some compounds, the accumulation of residues, etc. Packaging used for dispensing fragrance compositions comprising microcapsules and a volatile solvent are particularly prone to getting clogged. In addition, the mixing of the components in the pipe may not be completely satisfactory. Furthermore, the actuator assembly usually comprises several parts, to be assembled together, which therefore increases the complexity, the size and the cost of the manufacturing process of the spray dispenser.

There is therefore a need for providing a spray dispenser with side-by-side reservoirs providing an improved overall user's experience.

There is also a need for providing a spray dispenser with side-by-side reservoirs providing an improved spray performance over time, particularly a spray dispenser not getting clogged over time and being usable from the first to the last spray.

There is also a need for providing a spray dispenser with side-by-side reservoirs providing an improved mixing of the components, the composition therefore being homogeneously mixed upon dispensing.

There is also a need for providing a spray dispenser with side-by-side reservoirs comprising a simplified actuator assembly i.e. a simple, compact and/or cost-effective assembly, without compromising the user's overall experience.

There is also a need for providing an improved spray dispenser with side-by-side reservoirs for dispensing long-lasting fragrance compositions such as compositions comprising fragrance-loaded microcapsules and a volatile agent.

SUMMARY

Spray Dispenser

In a first aspect, the present invention relates to a spray dispenser for mixing a first and a second components into a sprayable composition, the spray dispenser comprising:

a first reservoir configured to hold the first component and a first pump unit being in
fluid communication with the first reservoir;
a second reservoir configured to hold the second component, being different from the first component, and a second pump unit being in fluid communication with the second reservoir;
a nozzle tip configured to spray the composition;
a common spray actuator operatively associated with the first and the second pump units and comprising a pipe;
wherein the pipe of the common spray actuator has a sinuous path and comprises a first inlet orifice, at one end, being in fluid communication with the first pump unit; one outlet orifice, at the other end, being in fluid communication with the nozzle tip; and a second inlet orifice, located between the first inlet orifice and the outlet orifice, being in fluid communication with the second pump unit; and
wherein the axis crossing both inlet orifices substantially perpendicularly intersects the axis of the spray direction passing through the outlet orifice and the nozzle tip.

The spray dispenser according to the present invention is a dispenser configured to separately hold two different components, while jointly dispensing them as a sprayable mixture (product). The spray dispenser may be configured to be grasped in one user's hand, preferably for the reservoirs to be grasped in one user's hand while the actuator assembly being actuated by one finger of the same hand e.g. the index finger. The size of the dispenser may then be such as to allow it to be handheld.

The spray dispenser according to the invention is advantageous in that the first and the second reservoirs are side-by-side; in that the spray actuator limits or even prevent the clogging from unmixed portions of the second component; and/or in that the spray actuator can be actuated by one finger for dispensing the given quantities of components.

The spray dispenser comprises a first reservoir, a second reservoir, a first pump unit, a second pump unit and an actuator assembly. The actuator assembly comprises a common spray actuator and a nozzle tip.

The common spray actuator is operatively associated with the first and the second pump units. The spray actuator comprises a pipe. As described herewith, the pipe has been designed in order to allow dispensing given quantities of the first component and the second component and mixing them as a homogeneous sprayable mixture (composition), while preventing clogging over time by the first and/or the second components, particularly by the second component. The inventor has designed a common spray actuator comprising one single dispensing pipe having a specific path and comprising three different orifices provided in a specific sequence and with a specific spatial relationship. To be specific, the pipe has a sinuous path and it comprises three different orifices i.e. a first inlet orifice at one end, one outlet orifice at the other end, and a second inlet orifice located between the first inlet orifice and the outlet orifice. The first inlet orifice is in fluid communication with the first pump unit. The second inlet orifice is in fluid communication with the second pump unit. The outlet orifice is in fluid communication with the nozzle tip. The spray device according to the present invention is particularly suitable for holding a second component, or comprising compounds, being usually prone to clog dispensing pipes.

The different elements of the spray dispenser—i.e. at least the first and the second reservoirs, the first and the second corresponding units and the actuator assembly—may be assembled together along a longitudinal axis (or main axis). In the present application, the other axis, when needed, are defined according to this longitudinal axis. Even though it is not mandatory, the spray dispenser may usually rest on a flat surface e.g. a table by the bottom sides of the reservoirs (or the casing if present). In such case, the longitudinal axis substantially is the vertical axis and the spray dispenser comprises from bottom to top the reservoirs, the pump units and the actuator assembly.

Reservoirs

The first component and the second component are hold respectively in a first reservoir and a second reservoir.

Each reservoir has an open end and may comprise a body and a neck. If necessary, for example if the body and the neck have differing cross-sections in size and/or in shape, the reservoir may also comprise a shoulder connecting the body to the neck.

The body delimits the inner volume for holding the component. The body may comprise at least one circumferential wall and a bottom side. In one embodiment, the bottom side is flat and allows the spray dispenser to rest on a flat surface.

The neck comprises an open end. The component may be supplied to the reservoir via the open end. After filling the reservoir, the neck is coupled to the corresponding pump unit in any suitable manner. For example, the neck may be coupled to the corresponding pump unit by threading, bonding, welding or click fastening. If necessary, a gasket, particularly airtight gasket, may be disposed between the neck and the pump unit.

The reservoirs may be fixedly coupled to the corresponding pump units. Hence, once the reservoirs are empty, the spray dispenser may be discarded. Alternatively, the reservoirs may be removably coupled to the corresponding pump units. Hence, once at least one of the reservoirs is empty, it may be refilled and coupled again to the pump unit or it may be replaced with a filled reservoir. Alternatively, one reservoir may be removably coupled to its corresponding pump unit, while the other reservoir may be fixedly coupled to its corresponding pump unit. Hence, only one reservoir may be changed, once emptied. Such embodiment may be useful for using a large non-replaceable reservoir with different replaceable reservoirs such as cartridges of smaller volumes.

Each reservoir may have a volume from 1 to 250 mL, preferably from 2 to 100 mL, more preferably from 5 to 25 mL.

The walls of each reservoir may be made of any suitable materials. The materials may be selected from the group consisting of ceramics, metal (for example aluminium), glass, resins, polymer-based materials (for example plastics) or composite material.

Each reservoir may have any suitable shape or design. In a preferred embodiment, the reservoirs have shapes allowing them to be assembled side-by-side. Particularly, the reservoirs may have complimentary shapes in order to be juxtaposed next to each other.

Each reservoir may substantially have a tubular shape extending longitudinally from the bottom to the top i.e. from its bottom side to its neck. Alternatively, each reservoir may have a substantially non-tubular shape such as a conic shape widening longitudinally from the bottom to the top of the reservoir or vice versa.

The cross-section of each reservoir may be any suitable cross-section such as circular, semi-circular, oval, semi-oval, square, rectangular, triangular, polygonal or star-shaped cross-sections.

At least one reservoir may have rigid walls. In such embodiment, the walls of the at least one reservoir are not elastically deformable, squeezable and/or shrinkable. In a preferred embodiment, both reservoirs have rigid walls. Alternatively, albeit not preferred, one of the two reservoirs or both reservoirs have non-rigid walls.

At least one reservoir has transparent walls. In one embodiment, both reservoirs are transparent. In another embodiment, one reservoir is transparent, while the other reservoir is not transparent e.g. the other reservoir is translucid or opaque.

The spray dispenser may comprise two separate, independent containers forming respectively a first reservoir and a second reservoir. In a preferred embodiment, both separate, independent containers are juxtaposed next to each other. In an alternative embodiment, one container may be placed within the other container.

The spray dispenser may only comprise one container comprising one separation wall thereby delimiting two different compartments forming respectively a first reservoir and a second reservoir.

In addition to the first reservoir and the second reservoir, the spray dispenser may comprise a casing for holding in place both reservoirs. The casing may cover in part or in full the reservoirs. The casing may have an open bottom end and/or a side window, from which the reservoirs are introduced.

At least one reservoir, and/or the casing if present, may comprise illustrations, instructions and/or any other type of information. Such illustrations, instructions and other type of information may be printed or engraved on the reservoir or stuck to it.

Sprayable Product and Components for Obtaining it

The sprayable product (sprayable composition) is obtained by the mixture of the first component and the second component which are separately and respectively hold in the first and the second reservoirs.

"Sprayable composition" means a composition comprising materials/ingredients suitable for topical application on mammalian keratinous tissue including skin and hair.

All percentages are weight percentages based on the weight of the sprayable composition and the components for obtaining it, unless specifically stated otherwise. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at about 25° C. and at ambient conditions, where "ambient conditions" means conditions under about one atmosphere of pressure and at about 50% relative humidity.

"Substantially free of" means an amount of an ingredient of 1% or less, preferably 0.1% or less, more preferably 0.01% or less, most preferably of 0%, by weight of the composition/component.

"Non-volatile" refers to those materials which are liquid or solid under ambient conditions and have a measurable vapor pressure at 25° C. These materials typically have a vapor pressure of less than about 0.0000001 mmHg, and an average boiling point typically greater than about 250° C.

"Volatile" as used herein, unless otherwise specified, refers to those materials that are liquid or solid under ambient conditions and which have a measurable vapor pressure at 25° C. These materials typically have a vapor pressure of greater than about 0.0000001 mmHg, alternatively from about 0.02 mmHg to about 20 mmHg, and an average boiling point typically less than about 250° C., alternatively less than about 235° C.

The first component and the second component have different formulations. In a preferred embodiment, the first component comprises a volatile solvent and the second component comprises microcapsules, particularly fragrance-loaded microcapsules.

Both components may be in a liquid form at standard conditions. By "standard conditions" is meant an ambient temperature from about 18 to about 25° C., preferably about 20° C. and at atmospheric pressure. In one embodiment, neither the first component nor the second component is in a powder form or a gaseous form at standard conditions.

The components may differ at least by the presence of at least one material and/or by at least one material being present in different proportions and/or their physicochemical properties e.g. different viscosities and/or by their visual appearance e.g. different colors or different degree of clarity and/or turbidity, etc. The second component may be, or may comprise compounds being, prone to clogging dispensing pipes. In contrast, the first component may prevent, or may comprise compounds preventing clogging of pipes.

Viscosity

Each component may have a viscosity from 20 to 3000 mPa·s$^{-1}$, preferably from 50 to 600 mPa·s$^{-1}$, more preferably from 50 to 220 mPa·s$^{-1}$. The viscosity is measured using a Brookfield DV-II, spindle 3 at 60 rpm (measured at 25° C.).

Components

The components may be stored separately purely for aesthetical reasons such as providing components with different visual appearances.

Alternatively, or cumulatively, the components may be stored separately for chemical reasons. One of the components may comprise a material being inherently instable under specific conditions e.g. exposure to light and/or air. In such circumstances, this component may be hold in an opaque reservoir and/or an airtight reservoir. Both components may also comprise materials being incompatible when formulated together e.g. being immiscible such as water-soluble and water-insoluble materials. In such circumstances, the aqueous component comprising water-soluble materials may be hold in one reservoir and the non-aqueous component e.g. an oily component comprising water-insoluble material may be hold in the other reservoir. One of the components may comprise one material being degraded by another material comprised in the other component. The components may comprise material chemically reacting together with mixed e.g. hair dyes in presence of oxidizing agents and alkalizing agents.

In one embodiment, the components are substantially free of a propellant and are not hold in pressurized reservoirs.

Volume Ratio

The sprayable composition may be formed for a mixture of the first component and the second component in a volume ratio from 90:10 to 10:90, preferably from 80:20 to 20:80, more preferably from 70:30 to 30:70.

Volatile Solvent

The first and/or the second component, preferably the first component, may comprise a volatile solvent or a mixture of volatile solvents. The sprayable composition, obtained upon mixing of the first and the second components, may comprise at least about 10%, alternatively at least about 30%, alternatively at least about 40%, alternatively at least about 50%, alternatively at least about 60%, alternatively at least about 70%, alternatively at least about 80%, alternatively at least about 90%, of a volatile solvent by weight of the sprayable composition. In one embodiment, the component consists essentially of a volatile solvent. The volatile solvents may be relatively odourless and safe for use on human skin. The volatile solvents may be chosen from the group consisting of $C_1$-C alcohols and mixtures thereof; preferably from the group consisting of ethanol, methanol, propanol, isopropanol, butanol, and mixtures thereof; more preferably ethanol.

Non-Volatile Solvent

The first and/or the second component, preferably the first component, may comprise a non-volatile solvent or a mixture of non-volatile solvents. The sprayable composition, obtained upon mixing of the first and the second components, may comprise at least about 10%, alternatively at least about 30%, alternatively at least about 40%, alternatively at least about 50%, alternatively at least about 60%, alternatively at least about 70%, alternatively at least about 80%, alternatively at least about 90%, of a non-volatile solvent by weight of the sprayable composition. In one embodiment, the component consists essentially of a non-volatile solvent. The non-volatile solvents may be relatively odourless and safe for use on human skin. The volatile solvents may be chosen from the group consisting of benzyl benzoate, diethyl phthalate, isopropyl myristate, propylene glycol, dipropylene glycol, triethyl citrate, and mixtures thereof.

Fragrance

The first and/or the second component, preferably the second component, may comprise a fragrance. As used herein, "fragrance" is used to indicate any odoriferous material(s). The term "fragrance" means a non-encapsulated fragrance, unless specifically stated otherwise. Any cosmetically acceptable fragrance may be suitable for use presently. The fragrance may be liquid or solid at room temperature. The fragrance may be a volatile or a non-volatile fragrance. The fragrance may be from synthetic origin or from natural origin, including from plant or animal origin. A wide variety of chemicals are known as fragrances. The fragrance may be chosen from the group consisting of alcohols, aldehydes, ketones, ethers, Schiff bases, nitriles, esters, alkenes and mixtures thereof. Suitable examples of alcohols, aldehydes, ketones, ethers, Schiff Bases, nitriles, esters and alkenes are disclosed in the U.S. patent application 2017/0065993 A1, published on Mar. 9, 2017, which is incorporated herein by reference. The fragrance may be pro-fragrances, such as a pro-fragrance chosen from the group consisting of acetal pro-fragrances, ketal pro-fragrances, ester pro-fragrances, hydrolysable inorganic-organic pro-fragrances, and mixtures thereof. When using a pro-fragrance, the fragrances may be released from the pro-fragrance in a number of ways, such as for example by hydrolysis, by a shift in an equilibrium reaction, by a pH-change, by enzymatic release or any suitable.

The fragrances may have a boiling point (BP) of about 500° C. or lower, alternatively of about 400° C. or lower, alternatively of about 350° C. or lower. The boiling points of many fragrances are disclosed in *Perfume and Flavor Chemicals* (Aroma Chemicals), Steffen Arctander (1969).

The ClogP value of the individual fragrance materials may be about −0.5 or greater. As used herein, "ClogP" means the logarithm to the base 10 of the octanol/water partition coefficient. The ClogP can be readily calculated from a program called "CLOGP" which is available from Daylight Chemical Information Systems Inc., Irvine Calif., USA or calculated using Advanced Chemistry Development (ACD/Labs) Software V11.02 © 1994-2014 ACD/Labs. Octanol/water partition coefficients are described in more detail in the U.S. Pat. No. 5,578,563 published on Nov. 11, 1996.

The sprayable composition, obtained upon mixing of the first and the second components, may comprise from 0.001 to 40%, alternatively from 0.1 to 25%, alternatively from 0.25 to 20%, alternatively from 0.5 to 15%, of a non-encapsulated fragrance, by weight of the sprayable composition.

Microcapsules

The first or the second component, preferably the second component, more preferably the second component comprising a fragrance, may further comprise microcapsules. At least part of the fragrance is encapsulated in the microcapsules. The microcapsules may be any kind of microcapsule known in the art. The microcapsules may have a shell and a core material encapsulated by the shell. The core material of the microcapsules may include a fragrance, as defined herein. The shells of the microcapsules may be made from synthetic polymeric materials or naturally occurring polymers. Synthetic polymers may be derived from petroleum oil, for example. Synthetic polymers may be chosen from the group consisting of nylon, polyethylenes, polyamides, polystyrenes, polyisoprenes, polycarbonates, polyesters, polyureas, polyurethanes, polyolefins, polysaccharides, epoxy resins, vinyl polymers, polyacrylates, and mixtures thereof. Natural polymers occur in nature and may often be extracted from natural materials. Natural polymers may be chosen from the group consisting of silk, wool, gelatine, cellulose, proteins, and mixtures thereof. The sprayable composition, obtained upon mixing of the first and the second components, may comprise from about 0.01% to about 45% of microcapsules, by weight of the sprayable composition.

The microcapsules may be friable microcapsules. A friable microcapsule is configured to release its core material when its shell is ruptured. The rupture may be caused by forces applied to the shell during mechanical interactions, for example during dispensing the component comprising them the pipe and the nozzle tip of the present spray dispenser.

The microcapsules may have a shell with a volume weighted fracture strength of from about 0.1 to about 15.0 mega Pascals (MPas), alternatively from about 0.8 to about 15.0 MPa, alternatively from about 5.0 to about 12.0 MPa, alternatively from about 6.0 to about 10.0 MPa, when measured according to the Fracture Strength Test Method as described in U.S. patent application 2017/0065993 A1, which is incorporated herein by reference, or any incremental value expressed in 0.1 MPa in this range, or any range formed by any of these values for fracture strength.

The microcapsules may have a median volume weighted particle size of from about 2 to about 80 µm, alternatively from about 10 to about 30 µm, alternatively from about 10 to about 20 µm, as determined by the Test Method for Determining Median Volume-Weighted Particle Size of Microcapsules as described in U.S. patent application 2017/0065993 A1, which is incorporated herein by reference.

The microcapsules may have various core material to shell weight ratios. The microcapsules may have a core material to shell ratio of about 70 to about 30%, alternatively about 75 to about 25%, alternatively about 80 to about 20%, alternatively about 85 to about 15%, alternatively about 90 to about 10%, alternatively about 95 to about 5%.

The microcapsules may have shells made from any material in any size, shape, and configuration known in the art. For example, the shells may include a polyacrylate material, preferably a polyacrylate random copolymer, more preferably a polyacrylate random copolymer having a total polyacrylate mass, including ingredients selected from the group including: an amine content of about 0.2 to about 2.0% of the total polyacrylate mass, a carboxylic acid content of about 0.6 to about 6.0% of the total polyacrylate mass, and a combination of an amine content of about 0.1 to about 1.0% and a carboxylic acid content of about 0.3- to 3.0% of total polyacrylate mass.

The microcapsules may have various shell thicknesses. The microcapsule may have a shell with an overall thickness of about 1 to about 300 nm, alternatively from about 2 to about 200 nm.

The microcapsules may also encapsulate one or more benefit agents. The benefit agents may be selected from the group consisting of cooling sensates, warming sensates, perfume oils, oils, pigments, dyes, chromogens, phase change materials, or any other suitable benefit agents known in the art. The microcapsules may also encapsulate a partitioning modifier. Suitable benefit agents and/or partitioning modifiers are disclosed in the U.S. patent application 2017/0065993 A1, which is incorporated herein by reference.

The shells of the microcapsules may comprise a reaction product of a first mixture in the presence of a second mixture comprising an emulsifier, the first mixture comprising a reaction product of i) an oil soluble or dispersible amine with ii) a multifunctional acrylate or methacrylate monomer or oligomer, an oil soluble acid and an initiator, the emulsifier comprising a water soluble or water dispersible acrylic acid alkyl acid copolymer, an alkali or alkali salt, and optionally a water phase initiator. Suitable amine monomers and emulsifiers are disclosed in the U.S. patent application 2017/0065993 A1, which is incorporated herein by reference.

Processes for making the microcapsules are well known. Various processes for microencapsulation, and exemplary methods and materials, are set forth in U.S. Pat. Nos. 6,592,990; 2,730,456; 2,800,457; 2,800,458; 4,552,811; and U.S. patent application 2006/0263518 A1, which are incorporated herewith by reference. The microcapsules may be spray-dried to form spray-dried microcapsules.

Carriers and Water

When the component comprises microcapsules, the component may also comprise a carrier for the microcapsules. Suitable carriers may be chosen from the group consisting of water, silicone oils, other oils (for example mineral oil and/or isopropyl myristate) and fragrance oils; preferably water. The carrier should not significantly affect the performance of the microcapsules. Volatile solvents, such as for example 95% ethanol, are not suitable carriers for the microcapsules.

The sprayable composition, obtained upon mixing of the first and the second components, comprising the microcapsules may also comprise from about 0.1 to about 95%, alternatively from about 5 to about 5%, alternatively from about 5 to about 75%, of a carrier, by weight of the sprayable composition.

In some embodiments, when one of the components, preferably the first component, comprising a volatile solvent and the other component, preferably the second component, comprising microcapsules are sprayed, the mixture of the first and second components obtained i.e. the sprayable composition comprises from about 0.01 to about 75%, alternatively from about 1 to about 60%, alternatively from about 0.01 to about 60%, alternatively from about 5 to about 50%, of a carrier, preferably water, by weight of the sprayable composition.

pH

The sprayable composition, obtained upon mixing of the first and the second components, may have a pH from about 2 to about 10, alternatively from about 3 to about 9, alternatively from about 4 to about 8.

Additional Agents

The first and/or the second component, preferably the second component, may also comprise a suspending agent, particularly a suspending agent for suspending the microcapsules and/or any other water-insoluble material dispersed in the component. The sprayable composition, obtained upon mixing of the first and the second components, may comprise from about 0.01 to about 90%, alternatively from about 0.01 to 15%, of suspending agents, by weight of the sprayable composition. Suitable suspending agents are disclosed in the U.S. patent application 2017/0065993 A1, which is incorporated herein by reference.

The first and/or the second component, may also comprise an additional agent selected from the group consisting of a colouring agent, particularly a colouring agent in the form of a pigment, an antioxidant, a ultraviolet inhibitor, cyclodextrins, quenchers, skin care actives and their mixtures thereof.

In some embodiments, the sprayable composition, obtained upon mixing of the first and the second components, comprises at least about 50%, alternatively at least about 75%, alternatively at least about 90%, of water, by weight of the component; from about 0.01 to about 90%, alternatively from about 0.01 to about 15%, alternatively from about 0.5 to about 15%, of a suspending agent, by weight of the sprayable composition; wherein the component is free of propellants, volatile solvents (such as ethanol), detersive surfactants or mixtures thereof; wherein the microcapsules comprise a first fragrance and a shell that surrounds said first fragrance. In some embodiment, the second component is substantially free of a wax, an antiperspirant, and mixtures thereof. In some embodiments, the sprayable composition, obtained upon mixing of the first and the second components, comprises about 20% or less, alternatively about 10% or less, alternatively about 7% or less, of the microcapsules, by weight of the sprayable composition.

Pump Units

The spray dispenser comprises two pump units being in fluid communication with the corresponding reservoirs.

The pump units may be different from each other or may be the same. In a preferred embodiment, both pump units are the same.

The pump units may be selected from any pump units suitable for dispensing a liquid product, which are customarily known. The pump unit may be a standard pump associated with a tube dipped into the component or, alternatively, the pump unit may be an airless pump associated with a piston. In a preferred embodiment, the pump unit is a standard pump associated with a tube dipped into the component.

Spray Actuator

The spray dispenser comprises an actuator assembly including a common spray actuator and a nozzle tip.

The common spray actuator is operatively associated with the first and the second pump units. The common spray actuator is associated to the pump unit in any suitable manner. For example, the common spray actuator may be associated to the corresponding pump unit by bonding, welding or click fastening. If necessary, a gasket, particularly airtight gasket, may be disposed between the inlet orifices of the pipe and the corresponding pump units.

The common spray actuator may be manually actuated by one finger only e.g. the index finger, while grasping the spray dispenser in one hand. Such type of spray actuators is conventionally called push buttons.

The axial depression operation of the common spray actuator i.e. towards the top of the reservoirs simultaneous actuates both pump units. The common spray actuator is configured to dispense given quantities of the first component and the second component, when actuated. The quantities of components dispensed, and the ratio between the quantity of the first component and the quantity of the second component dispensed, may vary depending the type of pump units used. For example, if both reservoirs have the same volume and both pump units are the same, the same quantity of the first component and the second component should be co-dispensed upon actuation of the common spray actuator, and the first reservoir and the second reservoir should be substantially emptied after the same number of actuations.

The spray actuator comprises a pipe. The pipe has been designed in order to allow dispensing given quantities of the first component and the second component as a homogeneous sprayable mixture, while preventing clogging over time by the first and/or the second components, particularly by the second component. The spray dispensers according of the present invention, and particularly the arrangement of the common spray actuator and its pipe, exhibit advantages in comparison to conventional dual reservoir spray dispensers, comprising two pump units, particularly those comprising a common spray actuator comprising a Y-shaped or a T-shaped piping system. Indeed, the actuation of conventional dual reservoir spray dispensers requires an increased force than a spray dispenser comprising only one pump unit, thereby rendering difficult actuating the spray actuator with one finger. In addition, conventional dual reservoir spray dispensers are prone to getting clogged, particularly if at least one of the two components tends to dry and/or to accumulate clogging residues when left in the pipe. Furthermore, conventional dual reservoir spray dispensers may have a reduced performance for mixing and spraying both components homogeneously.

Such advantages are achieved by designing a common spray actuator characterized in that it allows providing a spray dispenser, wherein the first and the second reservoirs are side-by-side; in that it limits or even prevent the clogging from unmixed portions of the second component; and it that the spray actuator may be actuated by one finger for dispensing the given quantities of components.

To be specific, the inventor has designed a common spray actuator comprising one single dispensing and mixing pipe having a specific path and comprising three different orifices provided in a specific sequence and with a specific spatial relationship.

The pipe comprises a first inlet orifice at one end, one outlet orifice at the other end, and a second inlet orifice located between the first inlet orifice and the outlet orifice. The first inlet orifice is in fluid communication with the first pump unit, the second inlet orifice is in fluid communication with the second pump unit and the outlet orifice is in fluid communication with the nozzle tip. This specific sequence allows obtaining a pipe therefore comprising only two different sections. A first section is formed between the first inlet orifice and the second inlet orifice, in which a given quantity of the first component is displaced towards the second inlet orifice, upon actuation. A second section is formed between the second inlet orifice and the outlet orifice, in which both given quantities of the first and the second components are mixed before being dispensed through the nozzle tip as a homogeneous spray. Contrary to Y-shaped or T-shaped piping systems, the disposition of the second inlet orifice between the first inlet orifice and the outlet orifice is advantageous in that, after actuation, no unmixed portion of the second composition is left in the pipe, thereby limiting or even preventing its clogging. In such configuration, the first component flushes the second component.

The inlet orifices and the outlet orifice are also spatially arranged so that the axis crossing both inlet orifices substantially perpendicularly intersect the axis of the spray direction passing through the outlet orifice and the nozzle tip.

Eventually, the pipe has a sinuous path running from the first inlet orifice via the second inlet orifice to the outlet orifice. This sinuous path—while allowing providing a dispensing device wherein no unmixed second component is left after use and while allowing the provision of side-by-side reservoirs—elongates the path of the portion of the first component and the mixture of the portions of both components, by comparison with Y-shaped and T-shaped piping systems.

By "sinuous" is meant a path only having linear and curved sections, without angular sections. In one embodiment, the first section between the first inlet orifice and the second inlet orifice has a semi-circular shape and the section between the second inlet orifice and the outlet orifice has a "s" shape, so that the pipe has a lookalike "question-mark" shape ("?-shape").

The pipe may have any suitable cross-sectional shape for example a circular or an elliptical cross-sectional shape. The surface of the cross-section and its size (greatest dimension, smallest dimension, average dimension, diameter, etc.) may vary or may be constant. In a preferred embodiment, the cross-sectional shape has no sharp corners, for avoiding the accumulation of compounds or residues, which may be prone to clogging the pipe. In a most preferred embodiment, the pipe has a constant cross-section all along its length. Alternatively, the pipe may have a varying cross-section along its length. For example, the cross-section of the first portion may be smaller (or bigger) than the cross-section of the second portion.

The common spray actuator may comprise a body and a skirt circumferentially extending downwards (towards the reservoirs). The body and the skirt may be a unitary construction or may be different parts assembled together. Likewise, the body may be a unitary construction or may be at least two parts assembled together. The provision of a unitary common spray actuator or alternatively of a multipart common spray actuator may be dependent to the manufacturing method used. For example, multi-part common spray actuators may be manufactured using conventional molding techniques, while unitary common spray actuators may be manufactured using additive manufacturing techniques, trivially known as 3D printing techniques.

In one embodiment, the pipe may be formed into the thickness of the body. In an alternative embodiment, the pipe may be a separate element, which is affixed to the body.

In one embodiment, a gap configured to receive the nozzle tip may be formed into the skirt. In an alternative embodiment, the gap may be formed into the thickness of the body.

The spray actuator may comprise guiding means associated with corresponding means of the reservoirs and/or the pump units, for stabilizing the assembly of the spray actuator and for avoiding any unwanted rocking phenomenon.

The spray actuator, and its constituting elements e.g. the body, the skirt and the pipe, may be made of any suitable materials. The materials may be selected from the group consisting of ceramics, glass, resins, polymer-based materials or composite materials.

Upon actuation, the spray actuator may dispense a volume of sprayable composition from 10 to 250 µL, preferably from 50 to 150 µL, more preferably from 70 to 100 µL.

Nozzle Tip

The spray dispenser also comprises a nozzle tip. The nozzle tip is in fluid communication with the dispensing pipe. Any conventional nozzle tip may be used.

The nozzle tip may comprise a swirl chamber for atomizing the composition obtained by the mixing of the first and the second components.

The nozzle tip is configured to spray the composition in a given direction. Considering the relative position of the outlet orifice of the pipe and its corresponding nozzle tip to the inlet orifices, the direction of the spray is substantially perpendicular to the axis intersecting the inlet orifices of the pipe. When standing in its resting position, the axis of the spray direction may be horizontal or may have a given angle for a horizontal axis of reference e.g. up to 30°.

The spray pattern may vary depending on the nozzle tip used and may either be narrow, medium or large. The shape of the spray pattern depends the application targeted.

System

In a second aspect, the present invention relates to a spray dispensing system comprising the spray dispenser as described above, a first component and a second component;

wherein the first component is hold in the first reservoir and the second component is hold in the second reservoir;

wherein the first and the second components are different from each other; preferably wherein the first component comprises a volatile solvent and the second component comprises microcapsules; and wherein, upon actuation, the first and the second components are homogeneously mixed and dispensed as a sprayable composition.

Kit

In a third aspect, the present invention relates to a kit comprising, as described in the first aspect, a spray dispenser module comprising a first pump unit, a second pump unit, a nozzle tip and a common spray actuator; at least one first reservoir, optionally filled with a first component, configured to be removably coupled with the first pump unit; and at least one second reservoir, optionally filled with a second component, configured to be removably coupled with the second pump unit.

Method

In a fourth aspect, the present invention relates to a method comprising the following steps:

providing a spray dispensing system comprising a spray dispenser filled with a first and a second components, as described in the first and second aspects;

actuating the common spray actuator for pumping and thereby homogeneously mixing given portions of the first and the second component for obtaining a sprayable composition; and spraying the obtained composition.

FIGURES

DETAILED DESCRIPTION

Figure 1:
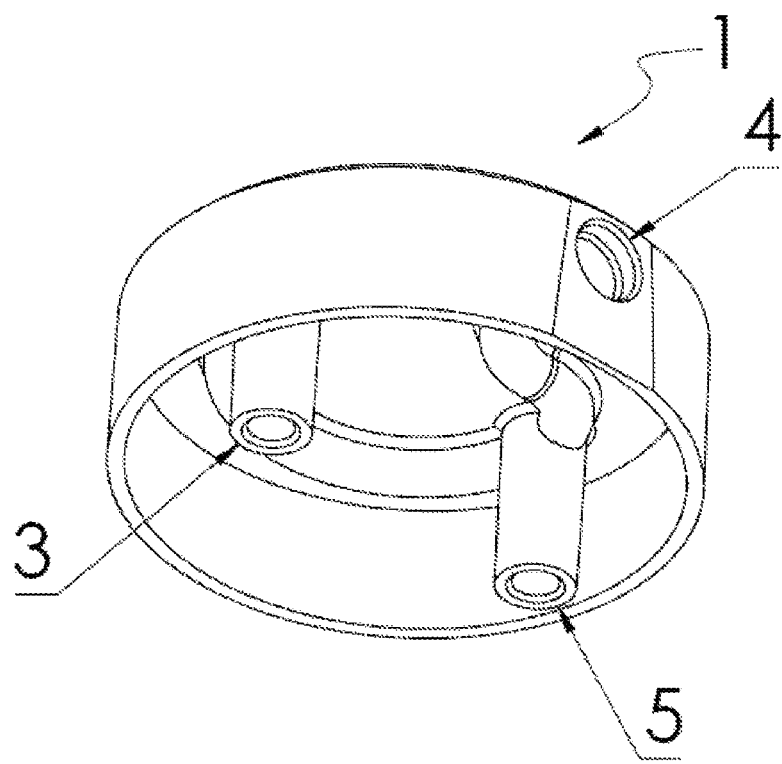
FIG. 1 represents a perspective view from bottom of the common spray actuator of the spray dispenser according to the present invention.
Figure 2:
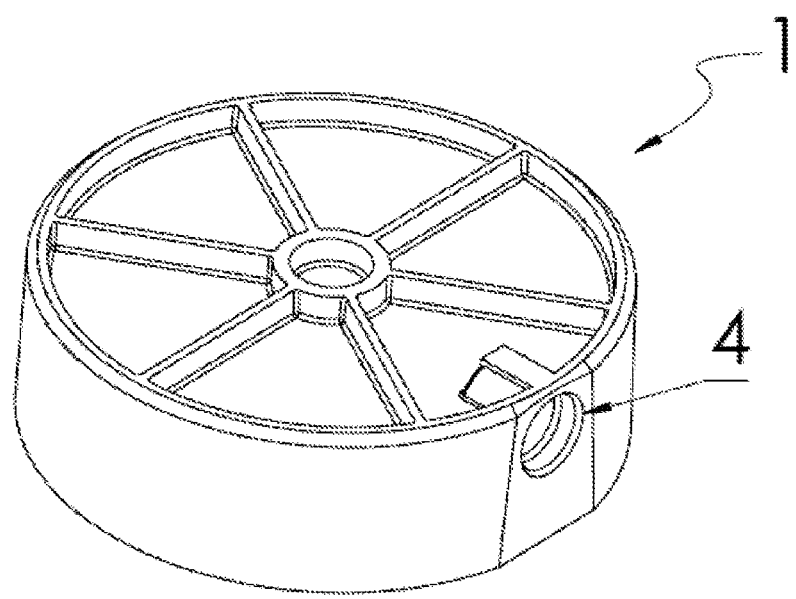
FIG. 2 represents a perspective view from above of the common spray actuator of the spray dispenser according to the present invention.

One embodiment of a common spray actuator 1 of the spray dispenser according to the present invention is shown in FIGS. 1 to 6, which should be construed as only being exemplary and not limitative. The common spray actuator as shown in FIGS. 1 to 6 is configured to be operatively associated with a first and a second pump units (not shown), which are themselves respectively in fluid communication with a first and a second reservoirs (not shown).

The common spray actuator comprises a pipe 2. The pipe 2 has been designed in order to allow dispensing given quantities of a first component and a second component and mixing them as a homogenous sprayable mixture, while preventing clogging over time by the first and/or the second components. The pipe 2 has a constant circular cross-section, forms a sinuous path and comprises three different orifices.

The pipe 2 comprises a first inlet orifice 3 having a circular cross-section, located at one end of the pipe 2. The first inlet orifice 3 is in fluid communication with the first pump unit.

The pipe 2 also comprises an outlet orifice 4 having a circular cross-section, located at the other end of the pipe 2. The outlet orifice 4 is in fluid communication with the nozzle tip (not shown).

The pipe 2 comprises a second inlet orifice 5 having a circular cross-section, located between the first inlet orifice 3 and the outlet orifice 4. The second inlet orifice 5 is in fluid communication with the second pump unit.

Figure 3:
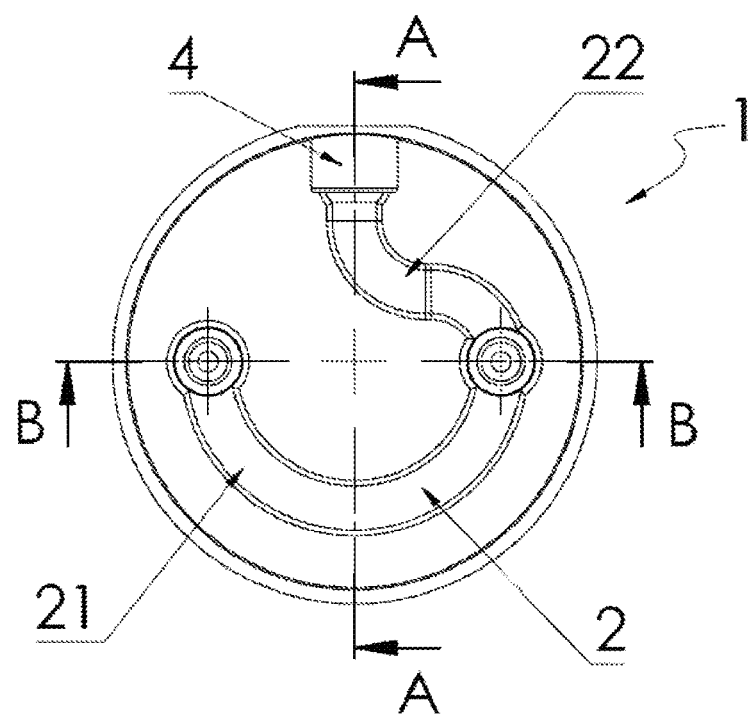
FIG. 3 represents a bottom view of the common spray actuator of the spray dispenser according to the present invention.
Figure 4:
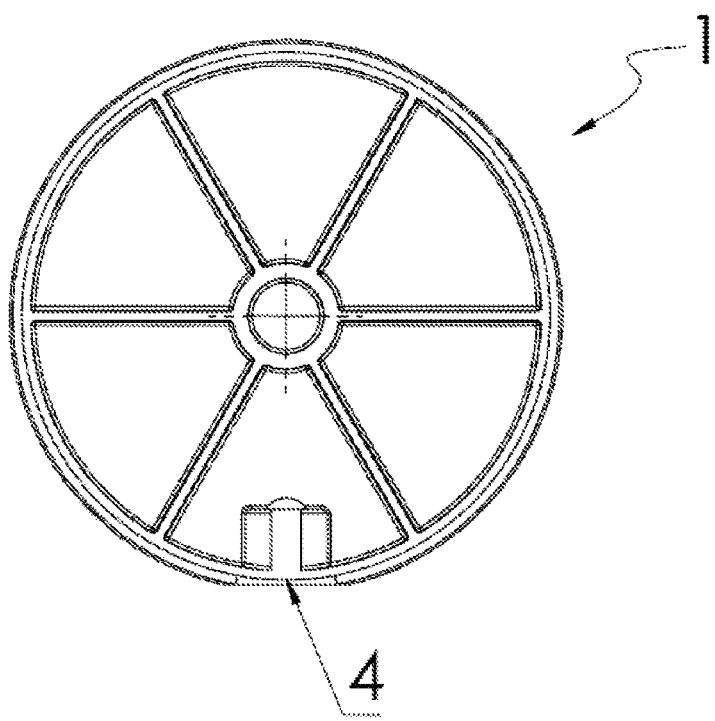
FIG. 4 represents a top view of the common spray actuator of the spray dispenser according to the present invention.
Figure 5:
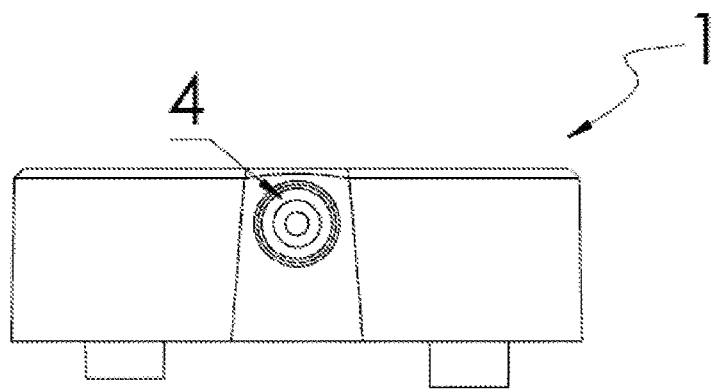
FIG. 5 represents a front view of the common spray actuator of the spray dispenser according to the present invention.
Figure 6:
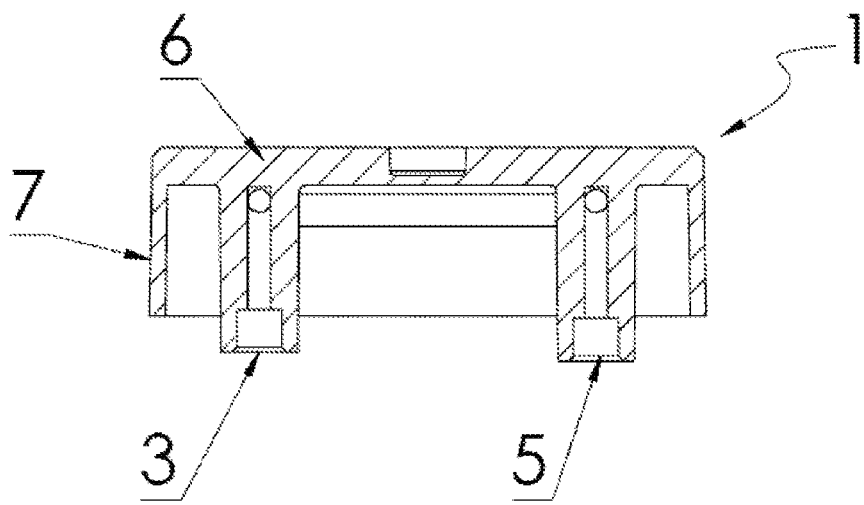
FIG. 6 represents a cross-sectional view of the common spray actuator of the spray dispenser according to the present invention, along the line B-B as shown in FIG. 3.
Figure 7:
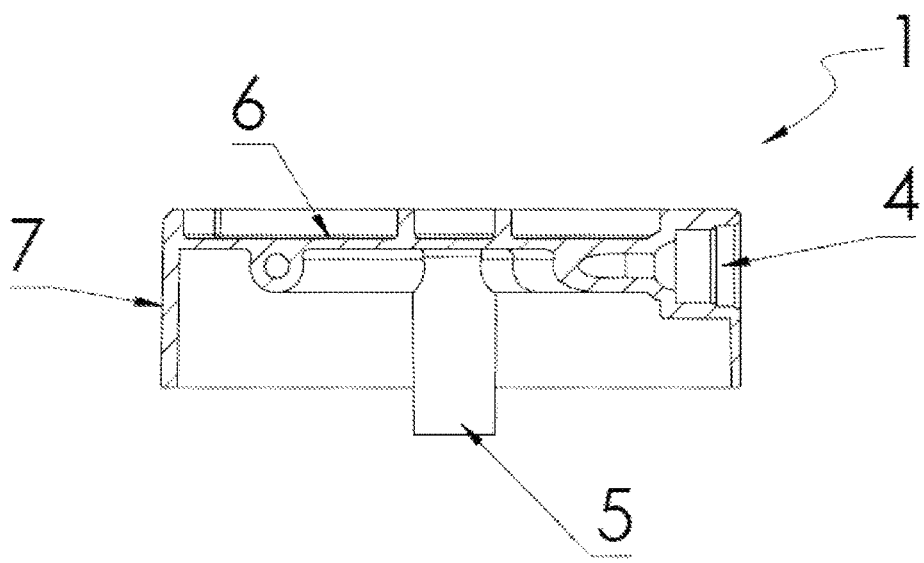
FIG. 7 represents a cross-sectional view of the common spray actuator of the spray dispenser according to the present invention, along the line A-A as shown in FIG. 3.

As shown in FIG. 3, the axis crossing both inlet orifices 3, 4 (represented as B-B) substantially perpendicularly intersects the axis of the spray direction (represented as A-A) passing through the outlet orifice 4 and the nozzle tip.

The pipe 2 particularly comprises two sections. The pipe 2 comprises a first section 21 formed between the first inlet orifice 3 and the second inlet orifice 5. A given quantity of the first component may be displaced from the first inlet orifice 3 towards the second inlet orifice 5, upon actuation. The pipe 2 also comprises a second section 22 formed between the second inlet orifice 5 and the outlet orifice 4. A given quantity of the first and the second components are mixed before being dispensed through the outlet orifice 4 (and the nozzle tip).

The first section 21 between the first inlet orifice 3 and the second inlet orifice 5 has a "C" shape (semi-circular shape) and the second section 22 between the second inlet orifice 5 and the outlet orifice 4 has a "S" shape, so that the pipe 2 has a lookalike "question-mark" shape.

The common spray comprises a body 7 and a skirt 8 circumferentially extending downwards. The body 7 and the skirt 8 forms a unitary construction. The pipe is formed into the thickness of the body.

Figure 8:
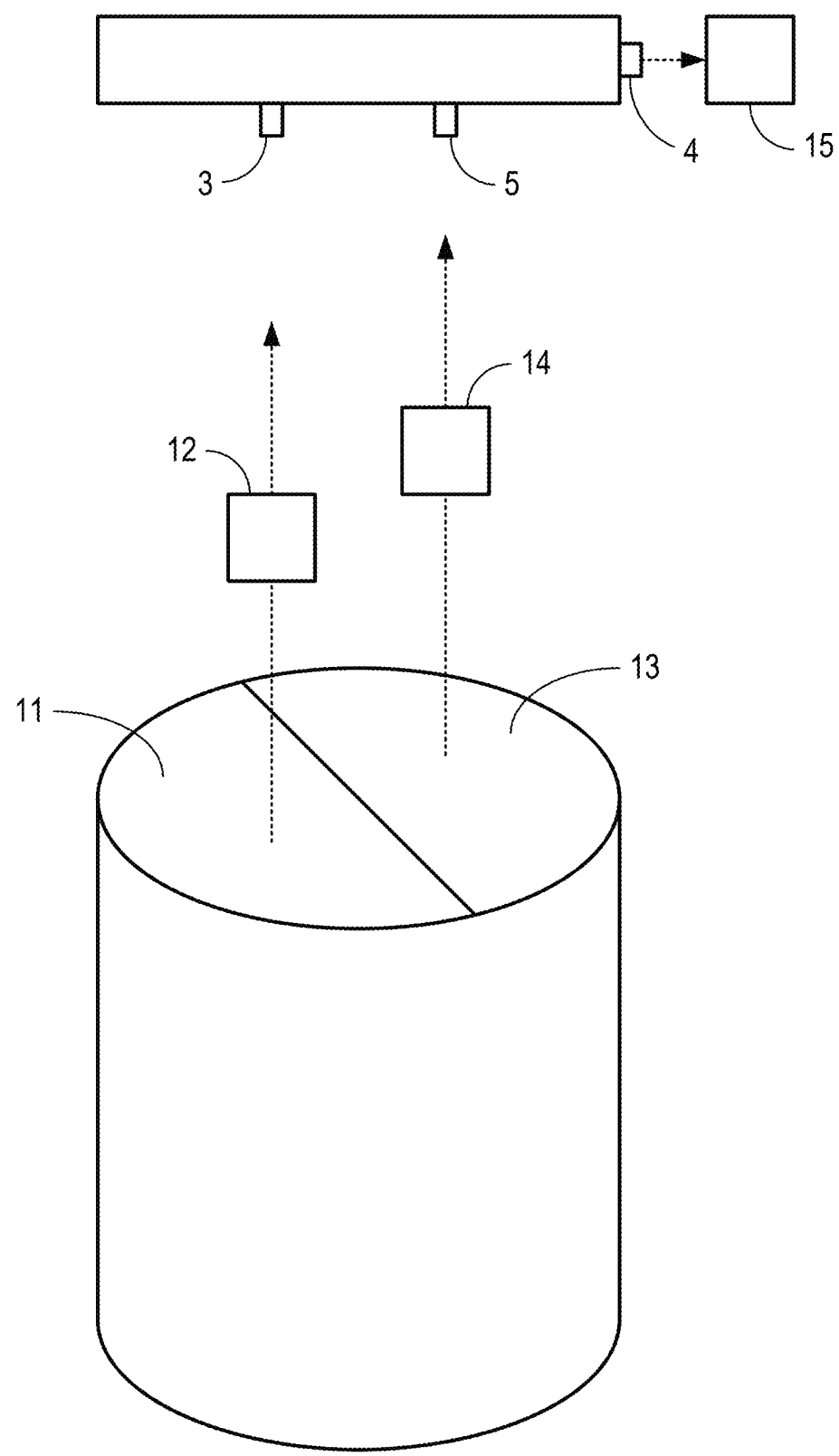
FIG. 8 represents a perspective view of an example of a spray dispenser system that is compatible with the common spray actuator of FIGS. 1-6.

FIG. 8 represents a perspective view of an example of a spray dispenser system that is compatible with the common spray actuator of FIGS. 1-6. A first reservoir 11 can hold the first component. A first pump unit 12 can be in fluid communication with the first reservoir 11. A second reservoir 13 can hold the second component. The second component can be different from the first component. A second pump unit 14 can in fluid communication with the second reservoir 13. A nozzle tip 15 can spray the sprayable composition. The common spray actuator can be operatively associated with the first pump unit 12 and the second pump unit 14.

Variations and modifications of the invention and further embodiments thereof, in addition to those described herein, will become apparent to those skilled in the art from the full contents of this document. The subject matter herein contains information, exemplification and guidance that can be adapted to the practice of this invention in its various embodiments and equivalents thereof. It is intended that the appended claims cover all such variations, modifications, embodiments and equivalents.

The invention is described with reference to various specific and preferred embodiments and techniques. However, it should be understood that many variations and modifications may be made while remaining within its scope. All referenced publications, patents and patent documents are intended to be incorporated by reference, as though individually incorporated by reference.

The invention claimed is:

1. A spray dispenser system for mixing a first component and a second component into a sprayable composition, the spray dispenser system comprising:
a first reservoir configured to hold the first component;
a first pump unit in fluid communication with the first reservoir;
a second reservoir configured to hold the second component, the second component being different from the first component;
a second pump unit in fluid communication with the second reservoir;
a nozzle tip configured to spray the sprayable composition; and
a common spray actuator operatively associated with the first pump unit and the second pump unit,
the common spray actuator comprising a pipe having a sinuous path,
a first end of the pipe having a first inlet orifice in fluid communication with the first pump unit,
a second end of the pipe, opposite the first end, having one outlet orifice in fluid communication with the nozzle tip,
the pipe having a second inlet orifice located between the first inlet orifice and the outlet orifice and in fluid communication with the second pump unit,
the first inlet orifice and the second inlet orifice defining an inlet axis,
the outlet orifice and the nozzle tip defining a spray direction axis,
the spray direction axis being perpendicular to the inlet axis, the pipe comprising a first section between the first inlet orifice and the second inlet orifice, the first section has a semi-circular shape, the pipe further comprising a second section between the second inlet orifice and the outlet orifice, and the second section has a "s" shape.

2. The spray dispenser system of claim 1, further comprising a container having a separation wall that delimits two different compartments to form respectively the first reservoir and the second reservoir.

3. The spray dispenser system of claim 1, wherein the common spray actuator comprises a body and a skirt circumferentially extending downwards.

4. The spray dispenser system of claim 1, further comprising the first component and the second component, wherein:
the first component is held in the first reservoir and the second component is held in the second reservoir;
the first component and the second component are different from each other; and
upon actuation of the common spray actuator, the first component and the second component are homogeneously mixed and dispensed as the sprayable composition.

5. The spray dispenser system of claim 4, wherein the first component and the second component are skin care components, hair care components, personal care components, grooming components, oral care components, health care components, fabric care components, or home care components.

6. The spray dispenser system according to of claim 4, wherein the first component and the second component are in a liquid form at standard conditions.

7. The spray dispenser system of claim 4, wherein the first component and the second component differ from each other by at least one of a presence of at least one material, a proportion of at least one material, at least one physico-chemical property, or a visual appearance.

8. The spray dispenser system of claim 4, wherein one of the first component or the second component comprises at least one of a material being inherently instable under determined conditions, a material being incompatible with another material comprised in the other of the first component or the second component, a material being degraded by another material comprised in the other of the first component or the second component, or a compound chemically reacting with another material comprised in the other of the first component or the second component.

9. The spray dispenser system of claim 4, wherein the first component comprises a volatile solvent or a non-volatile solvent.

10. The spray dispenser system of claim 4, wherein:
the second component comprises fragrances, microcapsules, and a suitable carrier; and
at least part of the fragrances are encapsulated in the microcapsules.

11. The spray dispenser system of claim 1, wherein:
the first reservoir is configured to be removably coupled with the first pump unit; and the second reservoir is configured to be removably coupled with the second pump unit.

12. A method, comprising
providing the spray dispenser system, according to of claim 4,
actuating the common spray actuator for pumping and thereby homogeneously mixing given portions of the first component and the second component for obtaining the sprayable composition; and
spraying the sprayable composition.

13. The spray dispenser system of claim 4, wherein the first component comprises a volatile agent, the volatile agent including at least one of ethanol, methanol, propanol, iso-propanol, or butanol.

14. The spray dispenser system of claim 10, wherein the second component further comprises at least one additional agent, the at least one additional agent being a suspending agent, a colouring agent, an antioxidant, an ultraviolet inhibitor, a cyclodextrin, a quencher, or skin care actives.

* * * * *